Figure 1:
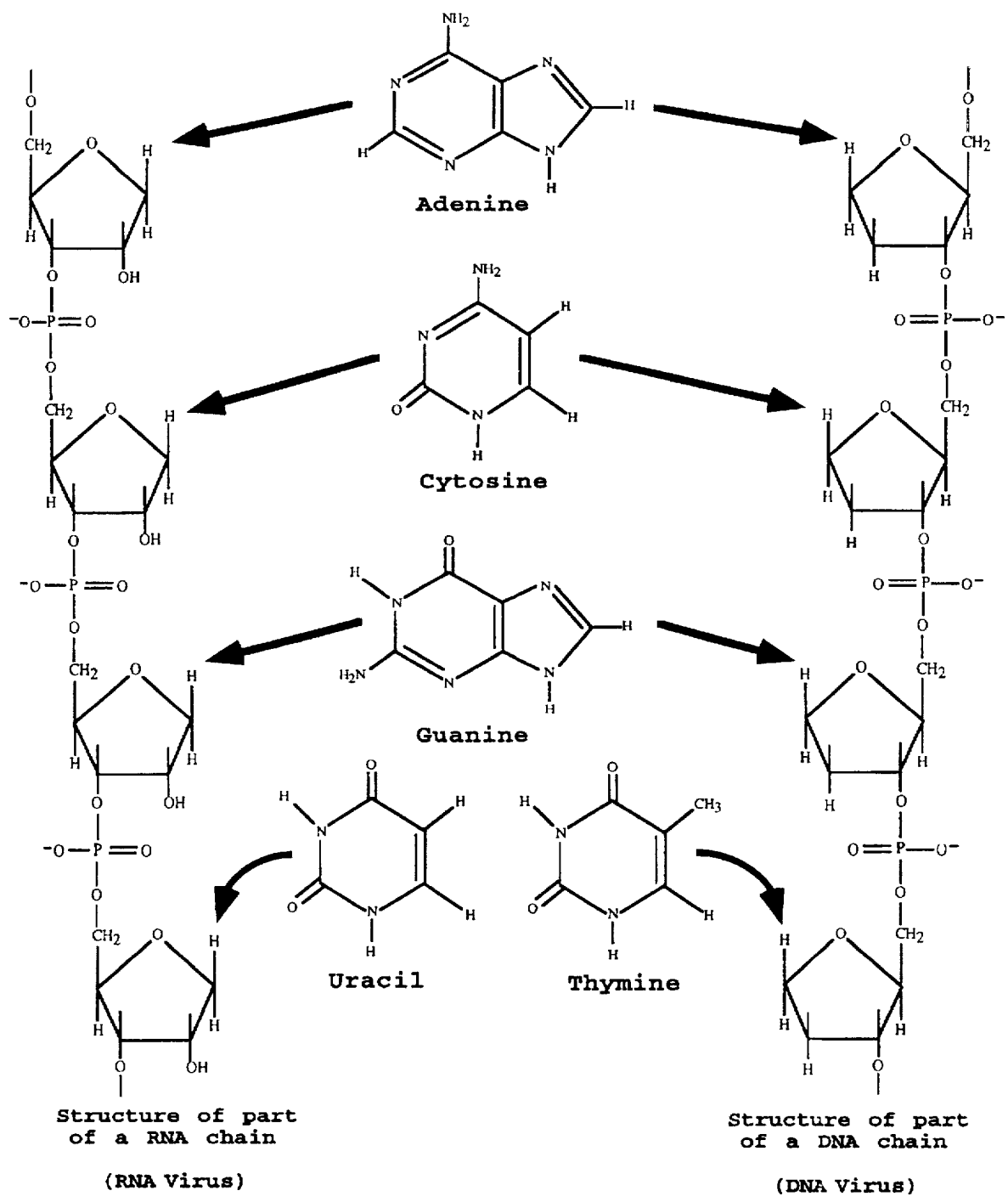

United States Patent [19]

Badaway

[11] Patent Number: 5,801,153

[45] Date of Patent: Sep. 1, 1998

[54] METHOD OF ENHANCING THE ANTIMICROBIAL PROPERTIES OF ANTIBACTERIAL ANTIBIOTICS TO MASSIVELY CONTROL AND PREVENT BACTERIAL, FUNGAL, AND VIRAL DISEASES IN PLANTS

[76] Inventor: Mohammed A. Badaway, 183 Cherokee Ave., Athens, Ga. 30606

[21] Appl. No.: 603,209

[22] Filed: Feb. 20, 1996

Related U.S. Application Data

[63] Continuation-in-part of Ser. No. 761,175, Sep. 13, 1991, abandoned.

[51] Int. Cl.[6] .......................... A01N 43/04; A01N 43/08; A61K 31/43
[52] U.S. Cl. .......................... 514/39; 514/197; 514/474; 514/565
[58] Field of Search .......................... 514/39, 197, 565, 514/474

[56] References Cited

PUBLICATIONS

Werner et al., C.A., vol. 96, (1982) 96:97143s.
Kawazu, C.A. vol. 117, (1992) 117:247160p.

*Primary Examiner*—Allen J. Robinson
*Attorney, Agent, or Firm*—James B. Middleton

[57] ABSTRACT

A method for controlling plant diseases utilizes a mixture of antibiotics and food additives or food preservatives. The mixture is sprayed on the plants twice per week for three weeks, then once every three weeks. Such a regimen has been found to cure plant diseases of bacterial, fungal and viral origin. The preferred form of the mixture has four ingredients, with the antibiotics and food additives in a ratio of from 1:1 to 1:3. The antibiotics are selected from amoxicillin trihydrate and neomycin sulfate, and the food additives are selected from sodium propionate, sorbic acid, potassium sorbate, caffeine, vanillin, ascorbic acid, L-Arginine, thymol, cupric sulfate and ammonium benzoate.

13 Claims, 2 Drawing Sheets

Structural differences between DNA and RNA viruses

Ascorbic Acid

Ribose

L-Arginine (open chain)

L-Arginine as pyrimidine ring

Pyrimidine ring

Orotic Acid

1

METHOD OF ENHANCING THE ANTIMICROBIAL PROPERTIES OF ANTIBACTERIAL ANTIBIOTICS TO MASSIVELY CONTROL AND PREVENT BACTERIAL, FUNGAL, AND VIRAL DISEASES IN PLANTS

CROSS-REFERENCE TO RELATED APPLICATION

This application is a continuation-in-part of the application by the same inventor, filed on Sep. 13, 1991, and having application Ser. No. 07/761,175 now abandoned.

BACKGROUND OF THE INVENTION

1. Field of the Invention

This invention relates generally to the treatment of plantdiseases, and is more particularly concerned with a method for effective treatment of numerous plant diseases and vectors that spread such diseases by treating plants with a mixture of substances from two different chemical groups of antimicrobial agents: antibacterial antibiotics and food preservatives.

2. Discussion of the Prior Art

When the bacteriostatic and fungistatic activities of antibiotics against pathogens were discovered, the search for safe replacement to control plant diseases had begun. It was found that the effectiveness and antimicrobial properties of antibiotics are pH dependent. There are some problems in applying antibiotics in agricultural fields as safe replacements:

1. The instability of antibiotics at pH 7, at which their molecules will be broken down;
2. Their effectiveness and antimicrobial properties do not last long as an aqueous solution because of their sensitivity to light and the pH problem;
3. Their application on plants has to be repeated in very short intervals (two days), making it a very expensive way to control plant diseases;
4. Antibiotics rely on having one active site to attack a pathogen, so plant pathogens can build up resistance to the antibiotics, resulting in the necessity to repeat application two to three times per week. The combination of two antibiotics has enhanced their performance, but has not solved the problem of controlling plant diseases.

In the food technology field, food preservatives have played a major role in protecting canned food. Their antimicrobial activities have reached ten-fold at acidic pH values, allowing reduction in concentration while still being effective to kill bacteria.

I-ANTIBACTERIAL ANTIBIOTICS

There are 11 groups of antibacterial antibiotics which are classified according to their physical and chemical properties. Two of them:

1. Aminoglycosides: They are bactericidal antibiotics derived from Actinomycetales. They are water soluble, stable, and inhibit the synthesis of protein by interference with the activity of ribosomes. There is a limitation to their use because of their ototoxic and nephrotoxic properties. Amikacin sulfate, Framycetin sulfate, Gentamycin sulfate, Kanamycin sulfate, Neomycin sulfate, Netilmicin sulfate, Paromomycin sulfate, Sissomycin sulfate, Tobramycin, Vancomycin hydrochloride, and Viomycin sulfate are the members of that family.

2. Penicillins: Penicillin was the first antibiotic to be used therapeutically. These are the most widely used antibiotics in the world. They are well tolerated to hypersensitivity reactions. The penicillin nucleus is composed of fused thiazolidine and Beta-Lactam rings with an amino group at the 6 position. Bacteriostatic and bactericidal antibiotics should not be normally combined because bacteriostatic antibiotics can inhibit the bactericidal property of penicillin (in a few cases the combination can be justified).

II-ANTIVIRAL ANTIBIOTICS

There are several antiviral agents whose functions are:

1. To be incorporated into DNA molecules and terminate their elongation, thus to prevent viral replication;
2. To inhibit DNA or RNA polymerase synthesis by competing with physiological substrates (nucleic acids subunits);
3. To block the assembly of viral envelopes (protein coat).

They are: Acyclovir, Idoxuridine, Flucystosine, Griseofulvin, Ketoconazole, Trifluridine, Vidarabine, Cyclophosphamide, Cytarabine, Rimantidine, Ribavirin, Acetylpyridinethiosemicarbazone, Bromodeoxyuridine, Fluoroidodoaracytosine, phosphonoformic acid and Rifamipin.

III-ANTIFUNGAL ANTIBIOTICS

Antifungal. antibiotics can be classified into six classes according to their mechanism of action. They are:

1. Inhibition of cell wall information (e.g. polyoxins);
2. Inhibition of cell membrane (e.g. polyenes, citrinin, and desertomycin);
3. Inhibition of Respiration (antimycin, patulin, pyrrolintrin, and flavensomycin);
4. Inhibition of Energy Transfer (e.g. oligomycin A, B, C, rutamycin, and venturicidin);
5. Inhibition of protein synthesis (e.g. cyclohexamide, blasticidin, streptomycin group, kasugamycin, and anisomycin);
6. Inhibition of Nucleic acid replication (e.g. phytoactin, griseofulvin, phleomycin, anthracyclines, and lomofungin).

Amoxicillin trihydrate

Amoxicillin trihydrate is an antibacterial antibiotic which is derived from several amino acids (Phenylalanine, cysteine, and valine). The structure of amoxicillin has a chemical importance in this combination. It has a free amino group, phenol ring which will decrease the number of local lesion, three double bonds (C=O) which will bond to the three phosphorous atoms of a pathogen's nucleic acids, one carboxyl group, and two methyl groups.

It was found that the 50% curing dose of amoxicillin is one-fifth of that of one ampicillin (Robinson 1974). It was effective against a wide variety of gram-positive and gram-negative bacteria. The bactericidal activities of amoxicillin combined with another antibiotic against "Entroccocci" bacteria was much greater than those of amoxicillin alone (Sutherland, 1976).

Neomycin Sulfate

Neomycin Sulfate is produced by "Streptomyces fradiae" bacteria. It is an amorphous base which is very soluble in water, methanol, and acidified alcohols. Neomycin is a bactericidal antibiotic which acts by inhibiting the synthesis of protein in susceptible bacteria. It is effective primarily against gram-negative bacteria. It reduces the number of ammonia forming bacteria in the intestinal tract. Neomycin has six amino groups, seven hydroxyl groups, three benzine rings, and one pentagon ring. All play an important role to maintain the pH of the composition.

Caffeine

Methylxanthines are known with their antimicrobial activities to control and inhibit a large number of bacteria and fungi. Caffeine (1.3.7 trimethylxanthine) has very important activities such as:

1. It inhibits DNA polymerase-I from "*Escherichia coli*" which is an important enzyme required for synthesis of DNA;
2. It inhibits aflatoxin production by *Aspergillus fungus*;
3. It has antimycotoxigenic activity;
4. It is involved in disturbing the normal biochemical function of the purine ring due to its ability to competitively block neurological adenosine receptors;
5. It inhibits the synthesis of phosphodiesterase enzyme, and thus prevents the activation of cyclic AMP;
6. It inhibits the activity of RNA-dependent DNA polymerase enzyme;
7. It uncouples the regulation of glycolysis and glycogenesis in "*S. cervisiae*" bacteria.

Ascorbic Acid

The chemical structure of ascorbic acid has an important role in both food technology and plant pathology:

1. It decreases the number of the local lesions of tobacco mosaic virus;
2. It has a structure similar to the ribose ring of the virus structure, and is considered as the best analogue to replace ribose or deoxyribose rings of RNA and DNA viruses;
3. It prevents the oxidation of polyphenoloxidase enzyme which has a major role in plant disease-resistance;
4. It plays an important role in keeping the quinones in reduced state, which may be the reason for developing the viral local lesions;
5. It succeeded in decreasing the pigmentations of tobacco mosaic virus.

L-Arginine

L-Arginine is one of the basic amino acids, and its chemical structure has an importance in curing several diseases:

1. It significantly reduces both rate, tumor induction, and the number of tumors induced by 7, 12 Dimethylbenz (a) anthracene;
2. It inhibits the carcinogenicity of acetamidie in rats;
3. It prevents ammonia toxication in adult cats, which is due to the anaplerotic effect of ornithine in the urea cycle; and, it enhances the detoxification of ammonia that arises from the degradation of the excess of other amino acids;
4. Arginine may change from open chain to pyrimidine ring by which it strongly competes for the pyrimidine sites of RNA and DNA structures;
5. Arginine can convert to orotic acid through metabolic reactions, and the orotic acid will compete for the pyrimidine sites of RNA and DNA structures.

Sodium Propionate

Sodium Propionate is one of the food preservatives that has antibacterial and antifungal activities. Its bacteriostatic activity is due to its interference with B-Lnine synthesis. It was found that the presence of adinine sulfate and biotin has a synergistic function with sodium propionate in inhibiting the growth of "*E. coli*" bacteria.

The structural similarity between propionic acid, alanine and certain other amino acids offers the possible mechanism of action of sodium propionate on the basis of substrate competition (Heseltin, 1952). The inhibition of bacterial or fungal growth is probably associated with the accumulation of sodium propionate within the cell and interference with the normal carbohydrate metabolism; the dehydrogenase system may be principally affected in this way.

Sorbic Acid and its Potassium Salt

Sorbic acid, an unsaturated fatty acid, is widely used as a food preservative. Its pKa is 4.76 to demonstrate its antimicrobial activity. It inhibits the synthesis of sulfhydryl enzymes, dehydrogenases (Whitakar, 1959; York, 1964), and catalase enzymes (Troller, 1965). It is involved in the depleting of ATP levels in the fungal conidia. It reduces extracellular accumulation of aflatoxins with 65% at concentration of 1000 µg/ml. The amount of phosphorous, potassium, and magnesium in total ash of fungal mycelia was reduced to one-third with the concentration of sorbic acid increased from 100 to 1000 µg/ml.

The effect of potassium sorbate versus sodium benzoate on decimal reduction time at 47° C. (thermal death time at 47° C.) was very impressive. A 50 µg/ml of potassium sorbate reduced the thermal death time from 25.3 to 16.3 minutes compared to 16.7 minutes when 500 µg/ml of sodium benzoate was used.

Thymol

Thymol is obtained from the essential oil of *Thymol vulgaris* L. and *Monarda puncata*. It occurs in other volatile oils. It has an important: role in food technology and medicine as follows:

1. It is used as an antifungal preservative;
2. It has antibacterial activity against periodontopathic bacteria;
3. It has an important role in inhibiting the dental diseases;
4. It has a role in active early diagnosis of viral hepatitis A;
5. It has a fast effect to reduce the level of mutans Streptococci in saliva;
6. It inhibits inositol-triphosphate binding activity;
7. It reduces the growth of *Salmonella typhimurium*;
8. It has a great antagonistic effect against Staphylococcus aureus under anaerobic conditions;
9. It has a useful antioxidant property which is considered as a natural replacement for synthetic antioxidant food additives;
10. It enhances the activity of some important enzymes such as alph-amylase, alkaline phosphatase, alanine aminotransferase;
11. It has a strong inhibitory effect on the polymerization of methyl methacrylate;
12. It inhibits the polymerization of hemoglobin S which causes sickle cell anemia;
13. Thymol is the least toxic agent among the endodontic compounds.

To increase the effectiveness of food preservatives (lipophilic acids), this requires:

1. pH value in acidic range;
2. Long chain of lipophilic compounds; and
3. Higher concentration increases the effectiveness up to ten-fold.

Lipophilic acids, including preservatives, apparently inhibit bacterial or fungal growth by inhibiting the cellular uptake of amino acids, organic acids, and phosphates. The lipophilic acids are correlated with the concentration of ATP molecules. Some of the food preservatives that are least harmful to human health, such a nitrite and sulfite, cause mutations and carcinogenic nitrosamines.

SUMMARY OF THE INVENTION

The present invention provides a stable composition with a pH value of approximately 5.2–5.3, to prevent and control plant diseases caused by bacteria, fungi, and viruses. It also provides a method to repel plant virus vectors.

The invention is based on a 4-ingredient formula, and comprises a mixture of antibiotic compounds and food preservative compounds in a ratio of 1:1 and 1:3. The composition is capable of preventing and controlling plant disease agents for about four weeks with one application.

The most effective and successful treatment for controlling diseases with very short time, and less expensively, is one which contains a wide variety of active sites to massively control the pathogens without leaving any possibility for resistance.

The selection of antibiotics and food preservatives for use with the present invention has been done according to the following facts:

1. The chemical structure to match what a plant pathogen needs for replication and reproduce the symptoms;
2. Antimicrobial properties which are based on:
   a. Minimum concentration that kills at least 50% of the pathogens;
   b. pH values and their antimicrobial activities;
   c. Long-term effectiveness;
   d. Antagonism;
3. Stereo chemistry.

The chemicals involved in this invention have been applied separately in the fields of both food technology and plant pathology. Each of them did a part of the job to reduce the number of local lesions caused by plant pathogens. When they were combined, the results were extremely impressive:

1. It is effective for four weeks per application compared to the toxic chemicals which is applied once every ten days.

2. It reduces the number of required applications to one-half or one-third.

3. It increases the intervals between applications to up to three to four weeks. This will lower the cost of application to one-third per acre.

4. It significantly enhances the performance of antibiotics and effectively controls the pathogens against which they have no activities.

5. It reduces the required amount of antibiotics to one-fourth per application.

6. It has a perfect pH value (5.2–5.3). This is a perfect pH for both food preservatives which can reach ten-fold of activity and antibiotics which can reach the stability and maximum activity as well as plants which can tolerate that pH without phytotoxicity. If we mix the four ingredients with the perfect concentrations as described in the invention, the pH meter will read 5.2–5.3. So, there is no need to add any buffer to maintain the pH of the composition.

7. It minimizes and eliminates the risk of life that applicators could face compared to the use of the toxic counterparts.

8. It is considered as a new and safe method to replace these toxic compositions to control plant diseases and their vectors.

9. It overcomes all the disadvantages of the commercial use of antibiotics in agricultural fields.

10. It protects our environment and other lives from the toxicity of spraying hazardous chemicals.

11. The combination of food preservatives and antibiotics offers a new technique to enhance the antimicrobial properties of antibiotics to control the pathogens against which they have no activities, and to overcome antibiotic-resistance problems. On the other hand, this will save millions of dollars which could be spent to create new antibiotic with slight effect on viruses, bacteria, or fungi.

The chemicals utilized are readily mixed with water to form an aqueous spray mixture having high bactericidal, fungicidal and viricidal activities, good weatherability and no phytotoxicity.

BRIEF DESCRIPTION OF THE DRAWINGS

These and other features and advantages of the present invention will become apparent from consideration of the following specification when taken in conjunction with the accompanying drawings in which:

FIG. 1 is a schematic illustration showing the structure of part of the chains of genetic material of viruses; and, FIGS. 2A—2F show the structure of some food additives and similar sites on genetic material.

DETAILED DESCRIPTION OF THE EMBODIMENTS

The antibiotics are multivalent bases, acids, or salts having an affinity for, or ability to react with, one or several molecules according to the numbers of hydroxyl, carboxyl, or amino groups, or double bonds that an antibiotic has to react with. Acidic or basic radicals are used to further control or adjust the pH of the composition to a desired level, and do not hurt the plant tissues nor destroy the stability of the antibiotics.

It is known that the effectiveness of an antibiotic combined with food additives (lipophilic and fatty acids) is partly dependent on the rate at which the compound diffuses into the infected plant tissues. Different solubilities of the components would affect the diffusion rate. In addition, the physio-chemical properties of the components similarly affect the application. Chemically combining the antibiotics and food additives would give them common physio-chemical properties, including a common diffusion rate, and would considerably simplify the control of application technique. The ratio between antibiotics and food additives is important to achieve a desirable application to the infected area. On the other hand, it is important to decrease the amount of antibiotic used, the number of applications required to control the diseased plants, and to shorten the term of application. It is a further objective to provide means for controlling the pH of the composition to stabilize the antibiotics, enhancing food preservatives' activities, equalizing the diffusion rate of the components and minimizing the toxic effect or the sensitivity to certain components of the composition not only for plant tissues, but also for the persons who apply it.

Another important objective is to provide a composition having a more effective control of the bacterial, mycoplasma, fungal, and viral plant pathogens than would be obtainable by spraying them separately.

The combination of food preservatives and antibiotics has made it possible to achieve the safest and the most secure way to prevent and control bacterial, mycoplasmal, fungal, and viral plant diseases, and to minimize the risk of human life as well as to protect the environment and the other lives from these highly toxic compositions which are, unfortunately, still widely applied.

EXAMPLE 1

Amoxicillin trihydrate (AT), Neomycin Sulfate (NS); as antibiotics, Ammonium Benzoate (AB), Sodium Propionate (SP), Sorbic Acid (SA), Potassium Sorbate (PS), Caffeine (C), Vanillin (V), Ascorbic Acid (AA), L-Arginine (AR), Thymol (TH), and Cupric Sulfate (CS) as food additives were tested. Both antibiotics and food additives are water soluble compounds. Sorbic acid, unsaturated fatty acid, is soluble in hot water and alkali (potassium hydroxide).

The effectiveness of 1-year-old concentrated composition (65 ml/gal) consisting of amoxicillin trihydrate, neomycin sulfate, caffeine, and potassium sorbate was tested. No toxic fungicidal or bactericidal compounds were used. The composition of antibiotics combined with food preservatives did not produce any toxic smell.

The pH of each antibiotic-food-preservative combination was tested. The pH meter read 5.2–5.3 and no buffers were added to maintain the composition's acidity. It is perfect for antibiotic's stability, food preservative's reaction, and for safety of plant tissues.

EXAMPLE 2

Aqueous solutions of the following formulations were used:

1. A solution composed of (AT) with concentration of $1.37\times10^{-3}$M/L.

2. A solution composed of (AT) with concentration of $2.74\times10^{-3}$M/L.

3. A solution composed of (AT) ($2.74\times10^{-3}$M/L)+(NS) ($1.79\times10^{-3}$M/L).

4. A gallon of concentrated solution (65 ml/gal) composed of (AT)+(NS)+(AB) with concentrations of $2.74\times10^{-3}$M/L, $1.79\times10^{-3}$M/L, and $7.18\times10^{-3}$M/L respectively (as 1-year-old solution).

5. A solution composed of (AT) ($2.74\times10^{-3}$M/L)+(NS) ($1.79\times10^{-3}$M/L)+(CS) ($2\times10^{-3}$M/L).

6. A solution composed of (AT) ($2.74\times10^{-3}$M/L)+(NS) ($1.79\times10^{-3}$M/L)+(V) ($303\times10^{-3}$M/L)+(C) ($5.15\times10^{-3}$M/L).

7. A solution composed of (AT) ($2.74\times10^{-3}$M/L)+(NS) ($1.79\times10^{-3}$M/L)+(V) ($3.3\times10^{-3}$M/L)+(SA) ($8.9\times10^{-3}$M/L).

8. A concentrated solution (60 ml/gal) composed of (AT) +(NS)+(C) with concentrations of $2.74\times10^{-3}$M/L, $1.79\times10^{-3}$ M/L and $5.15\times10^{-3}$M/L respectively.

9. 65 ml/gal of 1-year-old solution (#4)+(CS) ($2\times10^{-3}$M/L).

10. 60 ml/gal of concentrated solution #8 (AT+NS+C)+(CS) with concentration of $2\times10^{-3}$M/L.

11. 60 ml/gal of concentrated solution #8 (AT+NS+C)+(PS) with concentration of $6.66\times10^{-3}$M/L.

12. A solution composed of (AT)+(NS)+(SP) with concentrations $2.74\times10^{-3}$M/L $1.79\times10^{-3}$M/L, and $1.04\times10$M/L respectively.

13. A solution composed of (AT) ($2.74\times10^{-3}$M/L), (C) ($5.15\times10^{-3}$M/L), (AR) ($5.74\times10^{-3}$M/L), and (AA) ($5.68\times10^{-3}$M/L).

14. A solution composed of (AT) ($2.74\times10^{-3}$M/L), (NS) ($1.79\times10^{-3}$M/L), (C) ($5.15\times10^{-3}$M/L), and (TH) ($6.66\times10^{-3}$M/L).

EXAMPLE 3

Tests were performed as to the control of black spot fungus (*Diplocarpon rosae* ) attacking roses. The disease appeared in the middle of April and exuberated in later part of June until September every year depending on the prevailing humidity temperature, and rain.

Liming was done to neutralize the soil acidity and reduce a high level of free aluminum, iron, and manganese which are toxic to plants. On the other hand, calcium would increase the plant resistance to diseases and encourage better plant growth under the infection conditions.

The single application of amoxicillin at two different concentrations was applied. The results were poor to prevent the fungal infection of roses. The reaction of amoxicillin was slightly enhanced when it was combined with neomycin sulfate. Combining amoxicillin trihydrate ($2.64\times10^{-3}$M/L) with neomycin sulfate ($1.79\times10^{-3}$M/L) and ammonium benzoate ($7.18\times10^{-3}$M/L) had resulted in delaying the fungal infection of roses for two months when roses were sprayed twice between February 15 to March 15 for three consecutive seasons.

Two applications of a composition consisting of amoxicillin (AT), neomycin sulfate (NS) and ammonium benzoate (AB) were made between February 15 and March 17. Treated roses showed the first sign of infection after three months, and the infection of 40% of rose leaves occurred on the middle of September, compared to the control which were infected after six weeks and infection prevailed by the end of June each season.

Same results were obtained when sodium propionate or potassium sorbate was mixed with amoxicillin and neomycin.

It was demonstrated that the early two application of antibiotic-food preservative combinations on February 15th and March 17th of each season following with one application every four weeks had prevented rose infection by black spot fungus for the season.

A composition consisting of amoxicillin, neomycin, caffeine (C) ($5.15\times10^{-3}$M/L), and cupric sulfate (CS) ($2\times10^{-3}$M/L) resulted in shifting the composition from fungistatic to fungicidal activity.

The reapplication of antibiotic-food-preservative compositions was done once every four weeks compared to the toxic compositions such as; captan 50WP, mancozeb, maneb, microthiol, ziram, and orthenex which has to be repeated every ten days with a concentration which could exceed seven times that of one of antibiotic-food preservative's.

EXAMPLE 4

Tests were performed as to the control of brown spot fungus (*Septoira glycins*) attacking soy bean and fabae bean. The disease occurs in the second half of March (fabae bean) and last week of May (soy bean) and prevails in May (fabae bean) and in July to August (soy bean).

A composition of amoxicillin trihydrate ($2.74\times10^{-3}$M/L), neomycin sulfate ($1.79\times10^{-3}$M/L), sorbic acid ($8.9\times10^{-3}$M/L) and vanillin ($3.3\times10^{-3}$M/L) was made to control the fungal disease of beans. The composition had impressive fungicidal activity to massively react against the fungal colonies on the leaf surface without any phytoxicity.

There are some toxic composition such as; benlate 50 DF, bravo 720, topsin M 85 WDG, and thiabendazol which are applied every ten days to control the brown spot fungus. Some of these are very toxic.

EXAMPLE 5

Tests were performed as to the control of early blight and late blight (*Alternaria solani*) attacking potatoes and tomatoes. The disease is characterized by dark lesions with concentric rings, first evident on lower leaves. Early blight is favored by warm, wet weather. The severe infection occurs in August.

A composition consisting of amoxicillin trihydrate, neomycin sulfate, caffeine, and vanillin with concentrations of $2.74 \times 10^{-3}$ M/L, $1.70 \times 10^{-3}$ M/L, $5.15 \times 10^{-3}$ M/L, and $3.3 \times 10^{-3}$ M/L respectively, was made to control the fungal infection that causes early blight disease in tomatoes. Infected tomato plants were sprayed once every three weeks. The composition succeeded in suppressing the fungal infection. No fungal local lesions were developed during the three-week intervals nor after terminating the application.

Bravo W 75, Bravo 720, Bravo 500, Topsin M 85 WDG, Diathnane M 45, Ridonil, Bravo 81 W, and Terractro are the toxic counterparts which are usually recommended to control the fungal disease. Applications have to be repeated once every seven to ten days.

EXAMPLE 6

Tests were performed as to the control of Powdery mildew (*Erysiphe cichoracearum*) attacking cucumber and squash. The first sign of disease occurs in the middle of June and overflows in the later part of July.

A composition consisting of amoxicillin trihydrate, neomycin sulfate, caffeine, and potassium sorbate with fixed concentrations of $2.74 \times 10^{-3}$ M/L, $1.79 \times 10^{-3}$ M/L, $5.15 \times 10^{-3}$ M/L, and $6.67 \times 10^{-3}$ M/L respectively, was used to prevent and control powdery mildew in cucumber and squash. Applications were made every 4 weeks. Excellent epidemiological condition favorable for powdery milder disease prevailed in Spring-Summer 1991. The infection developed rapidly in control plots, while treated squash and cucumber plants showed no sign of infection. The fungal growth on the controls was washed off as a result of direct spray, but the fungal infection reappeared within four days. The composition had a mycostatic, not mycocidal, effect against the fungus.

Bravo 500, topsin M 70 W, bravo 900 DG, Bayleton 50 WP, and Topsin zm 85 WDG are the toxic compositions of the prior art to control the fungal disease of powdery mildew. Application have to be repeated every seven to fourteen days.

EXAMPLE 7

The discovery of electron microscopy was a giant leap to know more about plant diseases caused by viruses. The way viruses function in plants was the concern of all virologists. It was acceptable that viruses might function through the sequences of their nitrogen bases, purine and pyrimidine rings. Accordingly, virologists intensified their techniques to disturb the sequences of purine and pyrimidine rings of the structure of viruses as a way to stop their replications. The viral antibiotics industry has relied on that theory for more than four decades, and significant results had not yet been achieved.

Two purine rings (adinine, gaunidine), two pyrimidine rings (cytosine, uracil {RNA}, cystosine, thymine {DNA}), Sugar unit (ribose {RNA}, deoxyribose {DNA}), and triphosphate unit are the four important parts of viruses. As a result a 4-ingredient formula to substitute or replace all the four important parts of the structures should be effective in preventing viral replication. Looking at FIG. 1 of the drawings, it should be understood that:

1. Caffeine will compete for the purine rings—adenine and guanine
2. L-Arginine, as closed chain or orotic acid, will compete for pyrimidine rings—cytosine and thymine in DNA virus; cytosine and uracil in RNA virus
3. Ascorbic acid will compete for ribose in RNA virus, or deoxyribose in DNA virus
4. Amoxicillin will compete for triphosphate.

Figure 2A:
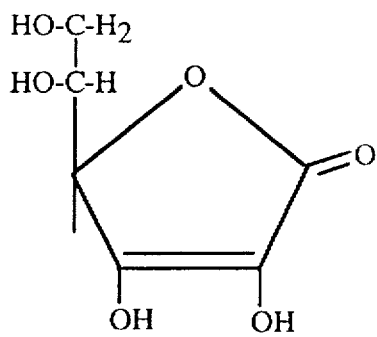
Figure 2B:
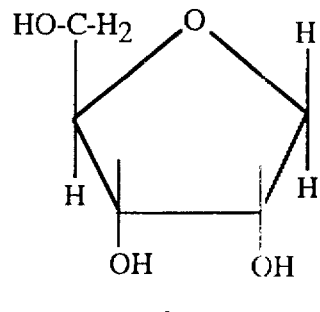
Figure 2C:
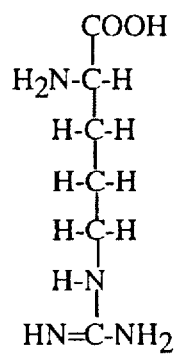
Figure 2D:
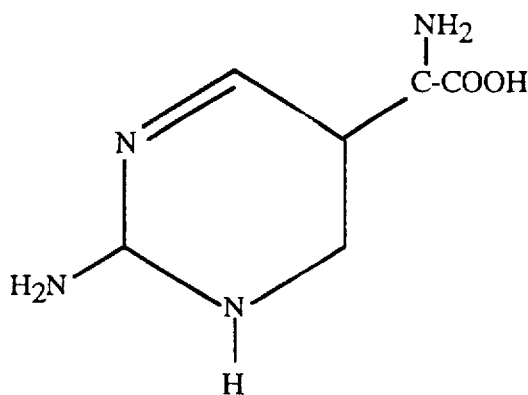
Figure 2E:
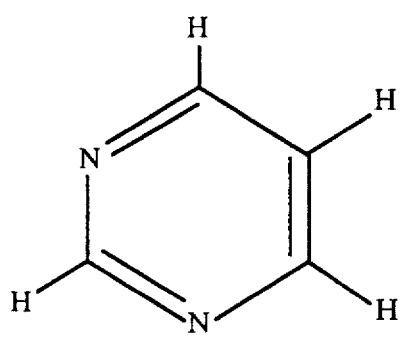
Figure 2F:
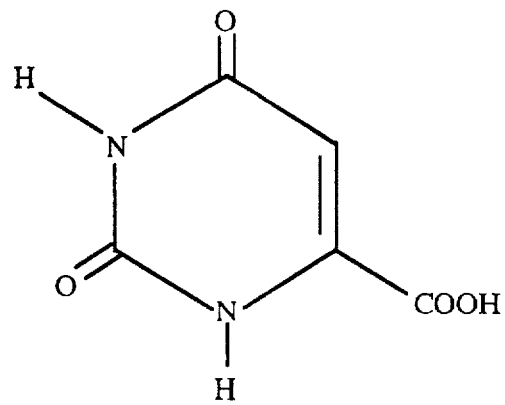

The mechanism may be better comprehended with attention to FIGS. 2A–2F where it can be easily seen that the ascorbic acid structure (FIG. 2A) is very similar to the ribose structure (FIG. 2B). Arginine (FIG. 2C) is a straight chain, but it can fold (FIG. 2D) to be similar to a pyrimidine ring, which is shown in FIG. 2E. Finally, FIG. 2F illustrates orotic acid, which can be a transformation of arginine, and which is very close to the pyrimidine ring of FIG. 2E.

Tests were performed to control potato leaf roll virus (PLRV) attacking green peppers and tomatoes, as well as potatoes, the principal host. PLRV is known as potato phleom necrosis virus, potato leaf curl, or net necrosis. It is one of the most serious viral diseases of potatoes. Four strains of PLRV were reported. Beet western yellow virus (BWYV) is often associated with potato leaf roll virus. The virus is small, isometric, and has icosahedral particles 24 nm in diameter. It is tuber borne and efficiently transmitted in a persistent manner by aphids. Green peach aphids, buckthorn aphids, potato aphids, and foxglove aphids are the vectors by which the virus can be transmitted.

The virus is spread over long distances by wind-borne aphids and over short distances by nonwinged aphids. Infections are always accompanied by phloem necrosis, and primary phloem cell wall in stem and petioles become thicker, starch accumulates in the leaf cell which causes leaf stiffness. The symptoms first appear about four weeks after planting, or when the host plants are about six inches high. Early season infection usually results in a characteristic rolling of the upper leaflets. A purple pigment may be developed at the base of young leaflets. The infected plants are often attuned and rigid. Secondary infection is more damaging to plants. The severity of the infection depends on the isolation of the virus, cultivar resistance, and growing conditions.

Potato leaf roll virus (PLRV) attacked 10-inch green pepper plants. The growth was completely stunted and leaves rolled upright for over 8 weeks. Breeding resistant cultivars, selection of disease-free seeds, and application of systemic insecticide to control aphids are the available ways to prevent a viral infection.

60 ml/gal of concentrated solution composed of amoxicillin trihydrate ($2.74 \times 10^{-3}$ M/L), neomycin sulfate ($1.79 \times 10^{-3}$ M/L), caffeine ($5.15 \times 10^{-3}$ M/L) and potassium sorbate were applied. The infected plants were sprayed twice/week for the first three weeks. A significant response took place as a sign of recovery.

Plants received three more application at three-week intervals. Applications were terminated. No reinfection by the same virus or another was detected during the three-week intervals, nor after terminating applications.

EXAMPLE 8

Cucumber mosaic virus (CMV) belongs to the cucumovirus group which has isometric particles 29 nm in diameter, each one being built from 180 identical amino acids with molecular weight of 24×10 daltons. They encapsulate four single stranded RNA molecules. RNA's 1, 2, and 3 are all required for infection while the fourth RNA is required for synthesis of virus coat protein. CMV is transmitted by numerous species of aphids. *Aphis gossypii* and *Myzus percicae* are the regular vectors of CMV. Cucumoviruses are not known to be transmitted by fungi or nematodes.

Tests were performed as the control of cucumber mosaic virus, which attacks tomatoes under selected field conditions that favor the occurrence of diseases.

A composition consisting of amoxicillin trihydrate, neomycin sulfate, potassium sorbate, and caffeine was applied twice per week with three more applications at three-week intervals. Ingredients were made at fixed concentrations $2.74 \times 10^{-3}$ M/L, $1.79 \times 10^{-3}$ M/L, $8.9 \times 10^{-3}$ M/L, and $5.15 \times 10^{-3}$ M/L respectively. A remarkable sign of plant recovery started with the end of the third week of the treatment. No sign of reinfection was observed or detected during the three-week interval, or three months after terminating the applications. No phytotoxicity was observed as a result of plants' sensitivity to the composition.

EXAMPLE 9

A group of 400 potted soybeans plants was divided into four experiments (G1, G2, G3 and G4) and four controls (C1, C2, C3 and C4), each having 50 plants. Both experimental and control groups were inoculated with viral particles of soybean mosaic virus (SMV), cowpea mosaic virus (CPMV), bean yellow mosaic virus (BYMV), and bean common mosaic virus (BCMV) respectively. The experiment was repeated for two consecutive years.

A composition consisting of amoxicillin trihydrate, neomycin sulfate, caffeine and potassium sorbate at fixed concentrations of $2.74 \times 10^{-3}$ M/L, $1.79 \times 10^{-3}$ M/L, $5.15 \times 10^{-3}$ M/L and $6.6 \times 10^{-3}$ M/L respectively, was applied twice a week for the first three weeks of the experiment. Plants were scheduled to receive three more applications at three-week intervals.

A remarkable response took place as a sign of plant recovery after the first three weeks. Most of the new leaves had no viral local lesions. Growth, blooming, and pod set was normal and perfect. No sign of deterioration or side effect was developed as a result of the composition's phytotoxicity. No viral local lesions were detected during the three-week intervals, nor three months after terminating applications.

The combination of antibacterial antibiotics and food preservatives has significantly succeeded in controlling the viral diseases in plants, with remarkable results within a short time, and with no phytotoxicity.

EXAMPLE 10

Tests were performed as to the control of Bean Curly Dwarf Mosaic Virus (BCDMV) attacking green beans.

Bean curly dwarf mosaic virus is caused by a strain of quail pea mosaic virus (QPMV-B). The virus causes a great reduction in bean yield and total loss can occur in some varieties that develop systemic or top necrosis. Rugosity and curling leaves are the main symptoms, while highly susceptible cultivars may show dwarfing, epinasty, and proliferation.

BCDMV belongs to a twelve-member comovirus group, all of which share the major properties of cowpea mosaic virus. The cytopathological changes that are associated with the infection by comoviruses are the large vesiculate inclusions which are seen in the cytoplasm where the infection provokes characteristic proliferation of membranes and visicles. The virus particles frequently crystallize in close-packed arrays which sometimes form monolayers. The arrays may be curled in the shape of scrolls, or may close upon themselves to form hollow tubes with a diameter of 80 nm.

The virus is transmitted by spotted and blanned cucumber beetles, Mexican beetles, and flee beetles. The beetles retain the virus particles for a few days following their acquisition from susceptible cultivars, mainly the growing weeds in the vicinity of bear plants.

The virus particles were transmitted to 435 bean plants. After developing the symptoms, plants were scheduled to be treated twice a week for the first three weeks. They received three more applications at three-week intervals.

A composition consisting of amoxicillin trihydrate (antibacterial antibiotic) and caffeine, ascorbic acid, and L-arginine (food additives and preservatives) was applied in the first three weeks, followed by a three-week interval. Plants received three more application at three-week intervals. The three-week interval is a very good time for the virus to reproduce itself and renew the symptoms. After the first three-week application, the new-forming leaves showed no viral symptoms. All the new leaves formed during and after the twelve-week treatment were healthy and had no viral symptoms. Applications were terminated for three months to evaluate the viricidal property of the applied composition. The treated bean plants were periodically checked for reinfection during the three-week intervals and three months after terminating the application The significant results of the two-consecutive-year research has demonstrated the powerful viricidal activities of the 4-ingredient composition which succeeded in curing the infected plants and eliminated the viral reinfection in a very short time.

EXAMPLE 11

Tests were performed as to the control of cowpea mosaic virus (CMV) attacking cowpea plants. The cowpea mosaic virus belongs to the comovirus group as is explained in Example 10.

The virus particles were transferred to 275 cowpea plants. As soon as symptoms developed, plants were treated twice/week for the first three weeks, followed with a three-week interval. They received three more application at three-week intervals.

A composition consisting of amoxicillin trihydrate ($2.74 \times 10^{-3}$ M/L), caffeine ($5.15 \times 10^{-3}$ M/L), ascorbic acid ($5.68 \times 10^{-3}$ M/L), and L-arginine ($5.74 \times 10^{-3}$ M/L) was applied. The virus-infected plants responded significantly to the treatment. The growing leaves were thoroughly checked for the possibility of reinfection during the three-week interval. No positive case was detected. The same procedure was followed during each interval of the last three applications. Results were extremely impressive. Application was terminated and plants were checked for three months.

The 4-ingredient composition had demonstrated its powerful antiviral properties to help the treated plants recover within three weeks of the 12-week experiments. It was demonstrated that the intensified application within the first three weeks had played a major role for a fast plant recovery.

EXAMPLE 12

The invention is based on the combination of antibiotics with food preservatives. Each single compound has a specific job or mechanism to control certain types of pathogens, each compound differing from the others to contribute to control of plant disease pathogens. Having only one active site, or chemical group, antibiotics are likely to become resistible by pathogens that cause diseases either to plants or to humans. Accordingly, applications have to be repeated within very short intervals, which is very costly. It is a huge challenge for antibiotics to be applied as safe replacement to control plant diseases.

Amoxicillin trihydrate, an antibacterial antibiotic, was created by reacting three different amino acids (phenyl alanine, cysteine, and valine), but has no activity against fungi or viruses. The same is true of neomycin sulfate. They have activity against: certain types of bacteria.

Antibacterial antibiotics are lacking the existence of certain chemical groups, or active sites, which have antifungal or antiviral properties to control or prevent fungi or viruses. To add these antifungal or antiviral active sites to an antibacterial antibiotic is an expensive process which greatly increases the prices of antibiotics.

The present: invention offers a great leap in overcoming this costly problem. Antibacterial antibiotics are combined with food preservatives to control fungal and viral diseases within a very short time, with less use of the required amount of antibiotics, and at three to four week-intervals. Such results have never been achieved with a single application of expensive antifungal or antiviral drugs.

Since food preservatives are ingested in significant amounts, with no interference with the human organ functions as judged by toxicity tests, it is a new and economical method to powerfully reactivate, rearm, the antibacterial antibiotics to be massively effective to control the pathogen against which they have no activity.

EXAMPLE 13

Being obligated parasites, viruses are usually dependent for survival on being able to spread from one susceptible plant to another fairly easily and frequently. Viruses are unable to penetrate the intact plant cuticle, but there must be mechanical damage to the leaf as in the mechanical inoculation and transmission by insects.

Invertebrate animals have a considerable interest in transmitting viruses that cause severe economic losses, while other viruses are shown to multiply in the vectors. This means of virus transmission is a complex phenomenon which involves the virus, vector, host plant, and environmental conditions.

Nematoda and Arthropoda are the main two members of the invertebrates that feed on living plants. Arthropoda has six classes, two of which have members that feed on living plants. They are Insecta and Arachnida I. Insecta:

There are 9 out of 32 orders of Insecta which have members that feed on living plants and might be possible vectors:

1. Collembola (chewing insects)
2. Orthoptera (chewing insects, it has 10 vectors )
3. Dermaptera (chewing insects)
4. Coleoptera (chewing insects, it has 30 vectors)
5. Lepidoptera (chewing insects)
6. Diptera (Larvae feed on living plants)
7. Hymenoptera (Larvae feed on living plants)
8. Thynsoptera (Thrips, it has 6 vectors that rasp and suck living plants)
9. Hemiptera (it has 280 vectors that suck living plants such as Aphids, Leafhoppers, White flies, Mealy bugs, etc.)

II. Arachnida

It has one out of eleven orders (Acarina) that feeds on living plants which includes mites and ticks. Eriophyidae and Tetranychidae are the two families which are known to transmit viruses.

Tests were performed related to the controlling and repelling of bean aphids (*Aphis fabae*), green peach aphids (*Myzus persica*), bean Leaf beetles (*Cerotoma trifurcata*), Japanese beetles (*Popillia japonica*), stripped blister beetles (*Epicauta vittata*), brown stink bug (*Euschistus servus*), leaffooted bugs (*Leptoglossus phyllopus*), squash bugs (*Anasa tristis*), and redbanded leafhoppers (*Graphocephala coccinea*) which attack most of the field and vegetable crops.

Five plots of soybeans (400 plants), 3 plots of green beans (150 plants), and 3 plots of squash (60 plants) were designed for this experiment for two consecutive years. Three plots of soybeans, two of green beans and two of squash were sprayed once every three weeks.

A composition consisting of amoxicillin trihydrate ($2.74 \times 10^{-3}$ M/L), neomycin sulfate ($1.70 \times 10^{-3}$ M/L), caffeine ($5.15 \times 10^{-3}$ M/L) and Thymol ($6.66 \times 10^{-3}$ M/L) was applied.

Thymol as a food preservative was dissolved in concentrated acetic acid then mixed with the other ingredients to provide a wide protection to the experimental plants. Thymol and acetic acid added a very nasty taste to all the leaves of the treated plants. On the other hand, the significant success of the combination of amoxicillin, neomycin sulfate, and caffeine to control viral diseases had an important role to kill and wash the virus particles off the vector's mouth. However, the composition had a remarkable effect which kills stripped blister beetles, japanese beetles, brown stink bugs and red banded leafhoppers, while succeeding in repelling the others and driving them to the control plants to feed. Plant leaves which were mechanically damaged by the feeding bugs and beetles had no viral local lesions.

It was demonstrated that the combination of antibiotics and food preservatives (additives) had provided another major protection for plants by repelling and controlling the most important vectors by which viruses can be transmitted to plants. On the other hand, this impressive achievement will play an important part as safe replacements to control and repel plant disease vectors as well as eliminate the wide use of insecticides and pesticides.

It will of course be understood by those skilled in the art that the particular examples and embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

I claim:

1. A method for treating diseased plants, comprising the steps of spraying said plants with a microbiocidal composition comprising an enhanced microbiocidally effective mixture of antibiotics and food additives or preservatives, said antibiotics and food additives or preservatives being in a ratio of from 1:1 to 1:3 wherein said antibiotics are selected from the group consisting of amoxicillin trihydrate and neomycin sulfate and said food additives or preservatives are selected from the group consisting of ammonium benzoate, sodium propionate, potassium sorbate, ascorbic acid, caffeine, vanillin, thymol, arginine, sorbic acid and cupric sulfate.

2. A method as claimed in claim 1, wherein said antibiotic consists of amoxicillin trihydrate and neomycin sulfate, and said food additives or preservatives consists of vanillin and caffeine.

3. A method as claimed in claim 1, wherein said antibiotic consists of amoxicillin trihydrate and neomycin sulfate, and said food additives or preservatives consists of vanillin and sorbic acid.

4. A method as claimed in claim 1, wherein said antibiotic consists of amoxicillin trihydrate and neomycin sulfate, and said food additives or preservatives consists of thymol and caffeine, to repel plant virus vectors.

5. A method as claimed in claim 1, wherein said antibiotic consists of amoxicillin trihydrate and neomycin sulfate, and said food additives or preservatives consists of cupric sulfate and caffeine, to control black spot fungus of roses.

6. A method as claimed in claim 1, wherein said antibiotic consists of amoxicillin trihydrate and neomycin sulfate, and said food additives or preservatives consists of potassium sorbate and caffeine, to control cucumovirus.

7. A method as claimed in claim 1, wherein said antibiotics consist of amoxicillin trihydrate and neomycin sulfate, and said food additives or preservatives consist of ammonium benzoate and cupric sulfate, to control black spot fungus of roses.

8. A method as claimed in claim 1, wherein said antibiotics consist of amoxicillin trihydrate and neomycin sulfate, and said food additive or preservative consists of caffeine, to prevent and control fungal diseases in plants.

9. A method as claimed in claim 1, wherein said antibiotics consist of amoxicillin trihydrate and neomycin sulfate, and said food additive or preservative consists of sodium propionate.

10. A method as claimed in claim 1, wherein said antibiotics consist of amoxicillin trihydrate and neomycin sulfate, and said food additive or preservative consists of ammonium benzoate, to prevent fungal diseases.

11. A method as claimed in claim 2, wherein said antibiotic consists of amoxicillin trihydrate, and said food additives or preservatives consist of caffeine, arginine and ascorbic acid, to control como viruses.

12. A method as claimed in claim 1, wherein said antibiotics consist of amoxicillin trihydrate and neomycin sulfate, and said food additives or preservatives consist of caffeine and vanillin, to control brown spot fungus.

13. A method for enhancing the antimicrobial properties of antibacterial antibiotics for treatment and control of plant diseases, said method comprising the steps of combining said antibiotics with food additives or preservatives to control fungal and viral pathogens against which they usually have no activity, said antibiotics and said food additives or preservatives being mixed in a ratio of from 1:1 to 1:3 wherein said antibiotics are selected from the group consisting of amoxicillin trihydrate and neomycin sulfate and said food additives or preservatives are selected from the group consisting of ammonium benzoate, sodium propionate, potassium sorbate, ascorbic acid, caffeine, vanillin, thymol, arginine, sorbic acid and cupric sulfate.

\* \* \* \* \*